United States Patent [19]
Mullins

[11] Patent Number: 5,879,377
[45] Date of Patent: Mar. 9, 1999

[54] TANNING POOL

[76] Inventor: Cheryl Mullins, Rte. 1, Box 126, Friendship, Tenn. 38034

[21] Appl. No.: 949,888

[22] Filed: Oct. 14, 1997

[51] Int. Cl.[6] ........................................................ A61F 7/00
[52] U.S. Cl. .................................................. 607/95; 5/421
[58] Field of Search .................................. 606/80, 94, 95, 606/90; 5/421, 636; 297/219.1, 228.12, 397

[56] References Cited

U.S. PATENT DOCUMENTS

| | | | |
|---|---|---|---|
| 266,788 | 11/1882 | DuBoise et al. | D24/38 |
| 267,430 | 12/1882 | Lee | D24/38 |
| 3,688,775 | 9/1972 | Raymann | 607/95 |
| 4,606,523 | 8/1986 | Statz et al. | |
| 4,964,183 | 10/1990 | LaForce, Jr. | 5/421 |
| 5,101,823 | 4/1992 | Smith | |
| 5,345,633 | 9/1994 | Harnish | 5/639 |

*Primary Examiner*—Michael Peffley
*Assistant Examiner*—Roy Gibson
*Attorney, Agent, or Firm*—Michael I. Kroll

[57] ABSTRACT

A tanning pool (10) comprising an elongated bed tray (12) to hold some cool water (14) therein. In a first instance, when the elongated bed tray (12) is placed upon the ground outdoors in sunlight and in a second instance, when the elongated bed tray (12) is placed upon a floor (16) within a building (18), under a tanning apparatus (20), a person (22) can lie down in the cool water (14) within the elongated bed tray (12) to get a tan in a fun, comfortable and safe manner.

12 Claims, 3 Drawing Sheets

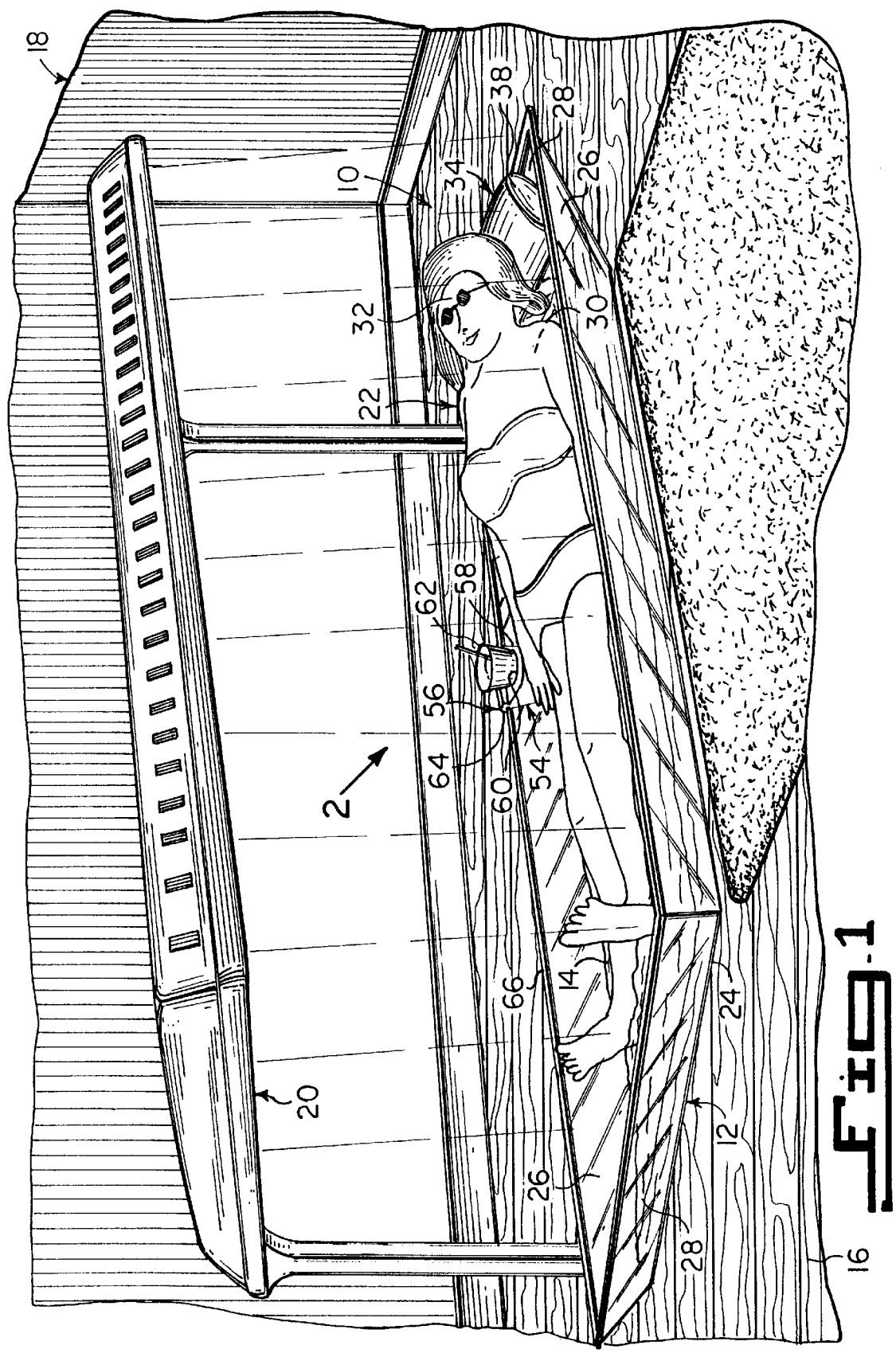

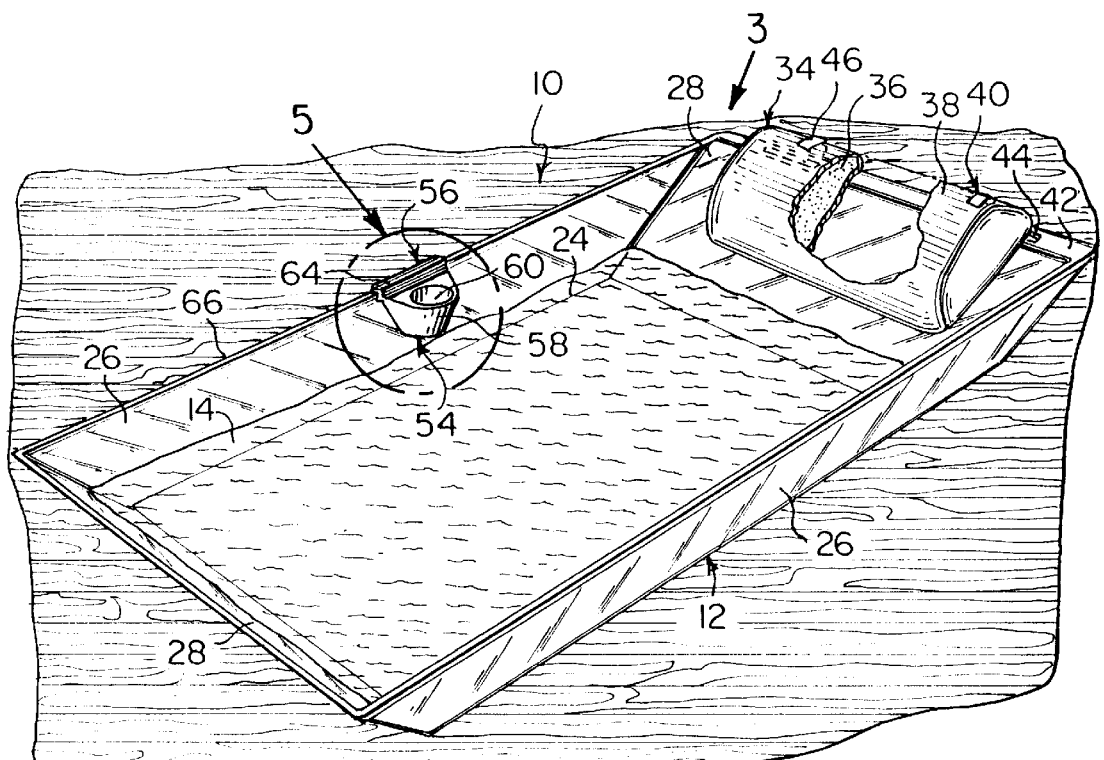
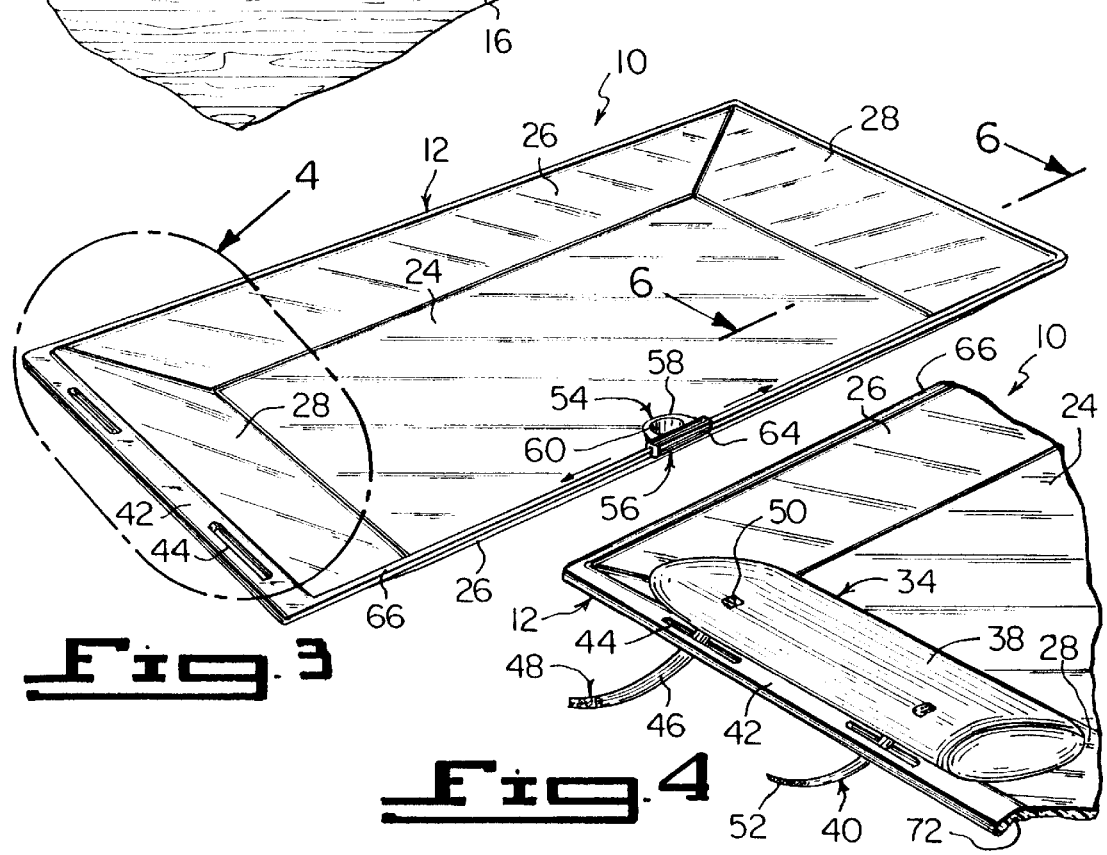

TANNING POOL

BACKGROUND OF THE INVENTION

1. Field of the Invention

The instant invention relates generally to tanning equipment and more specifically it relates to a tanning pool. The tanning pool is an elongated bed tray to hold some cool water therein, so that a person lying down in the bed tray can get a tan in a fun, comfortable and safe manner.

2. Description of the Prior Art

Ultraviolet radiation can produce direct and indirect effects upon the human body. The direct effects are limited to the surface skin because the rays have low penetrating power. Direct effects include sunburn, suntan, and progressive adaptation to heavier doses. Ultraviolet burns can be mild, causing only redness and tenderness, or they can be so severe as to produce blisters, swelling, seepage of fluid, and sloughing of the outer skin. The blood capillaries, which are tiny blood vessels, in the skin dilate with groups of red and white blood cells to produce the red coloration. A suntan occurs when the pigments in cells in the deeper, tissues portion of the skin are activated by ultraviolet radiation, and the cells migrate to the surface of the skin. When these cells die, the pigmentation disappears. The degree of pigmentation is directly related to the length of ultraviolet exposure and the body's inherent ability to produce pigments. Tanning is a natural body defense to help protect the skin from further injury.

Many people enjoy obtaining a golden tan in the warm summer months. The convenience of getting and maintaining that tan for some can be costly, unsafe and very uncomfortable. No everyone can afford a backyard pool, a pool membership, a tanning bed apparatus, which could prove to be unsafe, or have the convenience of a beach or lake. To lie down in a kiddie pool is very uncomfortable, while the inflatable mattress is subject to punctures and tears.

Numerous tanning equipment have been provided in prior art that are adapted to produce ultraviolet radiation, which will brown the skin of persons using the tanning equipment. While these units may be suitable for the particular purpose to which they address, they would not be as suitable for the purposes of the present invention as heretofore described.

SUMMARY OF THE INVENTION

A primary object of the present invention is to provide a tanning pool that will overcome the shortcomings of the prior art devices.

Another object is to provide a tanning pool that is an elongated bed tray to hold some cool water therein, so that a person lying down in the bed tray can get a tan in a fun, comfortable and safe manner.

An additional object is to provide a tanning pool in which the bed tray has an outwardly slanted end wall with a detachable pillow to support the back and head of the person, and an adjustable beverage cup holder on one outwardly slanted side wall to be used by the person lying down in the cool water within the bed tray.

A further object is to provide a tanning pool that is simple and easy to use.

A still further object is to provide a tanning pool that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein;

FIG. 1 is a perspective view of the present invention, showing a person lying down in cool water within an elongated bed tray, below a tanning apparatus on a floor within a building.

FIG. 2 is a perspective view taken in the direction of arrow 2 in FIG. 1, with the pillow broken away and the person and tanning apparatus removed therefrom.

FIG. 3 is a perspective view taken in the direction of arrow 3 in FIG. 2, of the present invention per se, with the pillow and water removed therefrom.

FIG. 4 is an enlarged perspective view of an area in FIG. 3 indicated by arrow 4, showing the pillow being installed thereon.

Similar reference characters denote corresponding features consistently throughout the attached drawings.

DETAILED DESCRIPTION OF THE PREFERRED EMBODIMENTS

Figure 5:
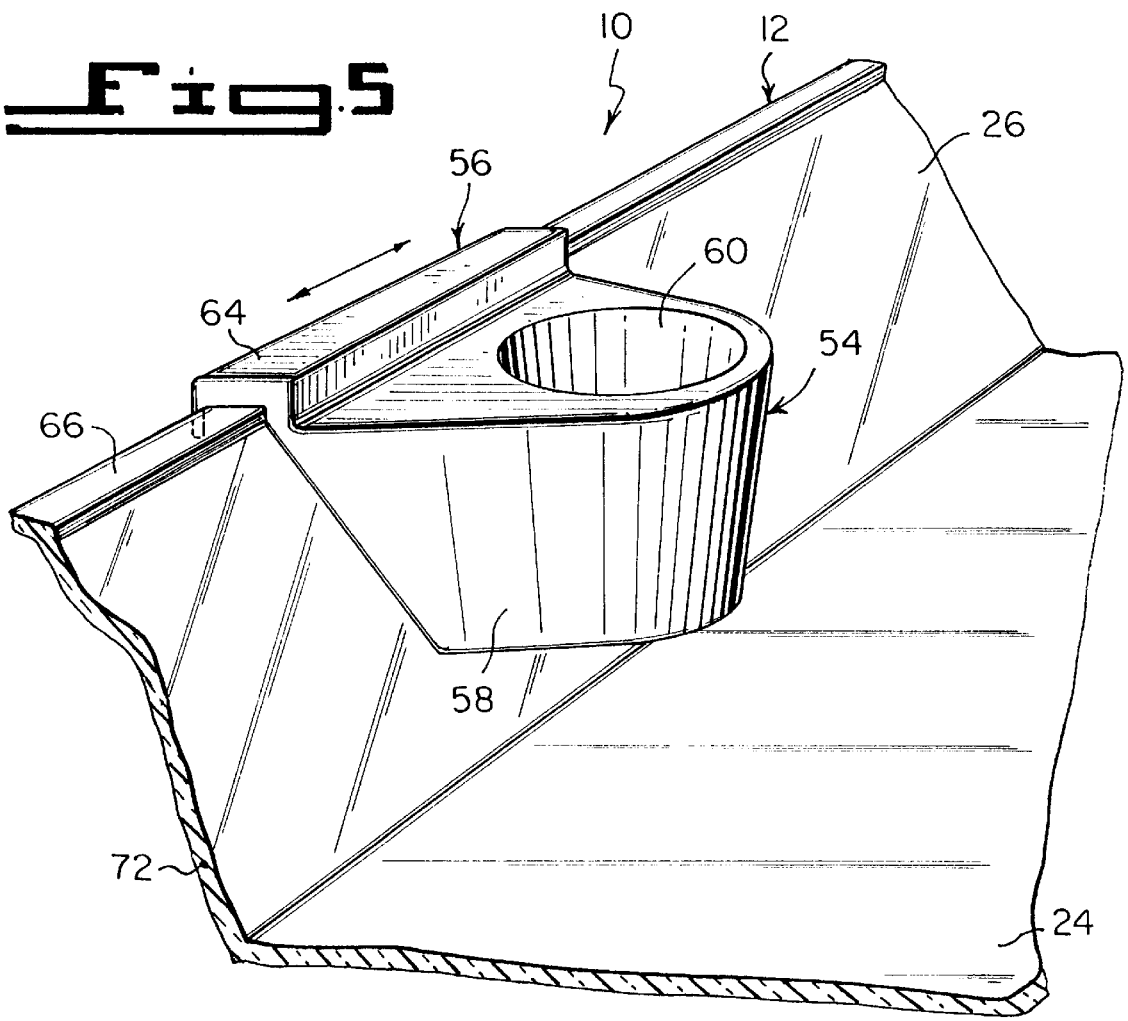
FIG. 5 is an enlarged perspective view of an area in FIG. 2 indicated by arrow 5, showing the adjustable cup holder in greater detail.

Turning now descriptively to the drawings, in which similar reference characters denote similar elements throughout the several views, FIGS. 1 through 6 illustrate the present invention being a tanning pool 10. With regard to the reference numerals used, the following numbering is used throughout the various drawing figures.

10 tanning pool
12 elongated bed tray of 10
14 cool water in 12
16 floor in 18
18 building
20 tanning apparatus
22 person
24 rectangular shaped bottom wall of 12
26 outwardly slanted side wall of 12
28 outwardly slanted end wall of 12
30 back of 22
32 head of 22
34 pillow
36 soft padding of 34
38 covering of 34
40 securing assembly for 34
42 flange on 28
44 slot in 42

46 strap on 34
48 VELCRO fastener
50 hook tab of 48
52 loop tab of 48
54 cup holder of 10
56 suspending structure for 54
58 housing of 54
60 top aperture in 58
62 beverage receptacle in 60
64 inverted U-shaped bracket for 56
66 top lip on 26
68 drain hole in 24
70 drain cap in 68
72 transparent durable hard plastic material for 12

The tanning pool 10 comprises an elongated bed tray 12 to hold some cool water 14 therein. In a first instance, when the elongated bed tray 12 is placed upon the ground outdoors in sunlight and in a second instance, as shown in FIG. 1, when the elongated bed tray 12 is placed upon a floor 16 within a building 18, under a tanning apparatus 20, a person 22 can lie down in the cool water 14 within the elongated bed tray 12 to get a tan in a fun, comfortable and safe manner.

The elongated bed tray 12 includes a rectangular shaped bottom wall 24 being of a size to accommodate the person 22. A pair of outwardly slanted side walls 26 are located at opposite long side edges of the bottom wall 24. A pair of outwardly slanted end walls 28 are located at opposite short end edges of the bottom wall 24. One of the outwardly slanted end walls 28 will support the back 30 and head 32 of the person 22 lying within the elongated bed tray 12 and be slanted slight enough to enable the person 22 to roll over and tan.

A pillow 34 supports the head 32 of the person 22 resting against the outwardly slanted end wall 28. The pillow 34 contains a soft padding 36 with a covering 38 and is of a size to extend across the outwardly slanted end wall 28 above the cool water 14 placed within the elongated bed tray 12.

An assembly 40 is for securing the pillow 34 to the outwardly slanted end wall 28. The assembly 40 consists of a flange 42 extending horizontally from a top edge of the outwardly slanted end wall 28. The flange 42 has two spaced apart slots 44 therethrough. A pair of straps 46 are spaced apart and attached to the pillow 34, so that the straps 46 can extend through the slots 44 in the flange 42. A pair of VELCRO fasteners 48 are provided. Each VELCRO fastener 48 contains a hook tab 50 attached to the pillow 34 and a loop tab 52 attached to a free end of one strap 46. The straps 46 can flip over the flange 42 and be attached in a removable manner to the pillow 34, to allow the pillow 34 to hang down on the outwardly slanted end wall 28.

The tanning pool 10 further contains a cup holder 54 and a structure 56 for suspending the cup holder 54 in an adjustable longitudinal manner on one of the outwardly slanted side walls 26 of the elongated bed tray 12. When the person 22 lies down in the cool water 14, the cup holder 54 will provide a beverage for the person 22. The cup holder 54 is a housing 58 having a top aperture 60 to receive a beverage receptacle 62 therein.

The suspending structure 56 includes an inverted U-shaped bracket 64 connected to the cup holder 54. The inverted U-shaped bracket 64 can slide upon a top lip 66 of the outwardly slanted side wall 26, to longitudinally adjust the cup holder 54.

Figure 6:
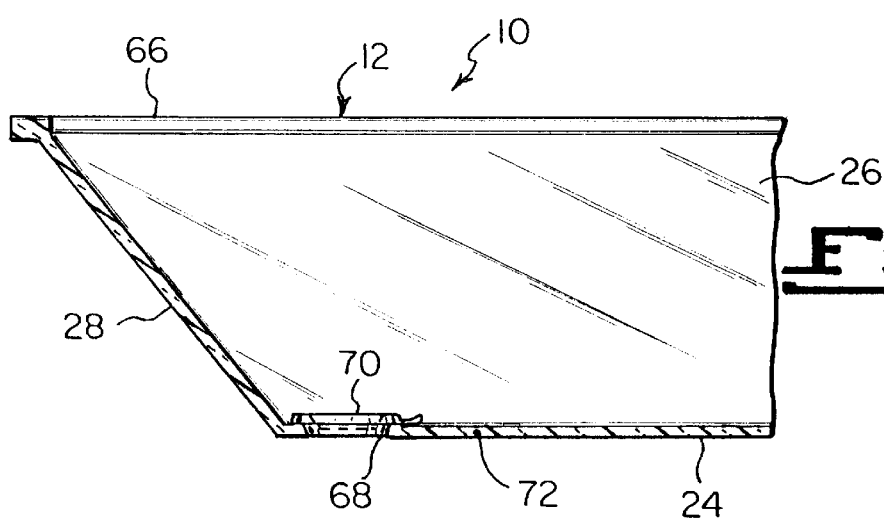
FIG. 6 is an enlarged cross sectional view taken along line 6—6 in FIG. 3, showing a removable drain cap mounted in a hole in the bottom wall.

The bottom wall 24 of the elongated bed tray 12 can have a drain hole 68 therethrough, as shown in FIG. 6. A drain cap 70 is placed in the drain hole 68. When the cool water 14 is to be drained therefrom, the drain cap 70 will be manually removed from the drain hole 68. The elongated bed tray 12 is fabricated out of a transparent durable hard plastic material 72, being sturdy enough to hold the cool water 14 therein, and light enough to store away and be used over and over again.

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A tanning pool comprising an elongated bed tray to hold some cool water therein, so that in a first instance, when said elongated bed tray is placed upon the ground outdoors in sunlight and in a second instance, when said elongated bed tray is placed upon a floor within a building, under a tanning apparatus a person can lie down in the cool water within the elongated bed tray to get a tan in a fun, comfortable and safe manner, wherein said elongated bed tray includes:

a) a rectangular shaped bottom wall being of a size to accommodate the person;
    b) a pair of outwardly slanted side walls located at opposite long side edges of said bottom wall;
    c) a pair of outwardly slanted end walls located at opposite short end edges of said bottom wall, whereby one of said outwardly slanted end walls will support the back and head of the person lying within said elongated bed tray and be slanted slight enough to enable the person to roll over and tan;
    d) a pillow to support the head of the person resting against said outwardly slanted end wall; and
    e) means for securing said pillow to said outwardly slanted end wall, said means for securing including;
        i) a flange extending horizontally from a top edge of said outwardly slanted end wall, said flange having two spaced apart slots therethrough;
        ii) a pair of straps, spaced apart and attached to said pillow, so that said straps can extend through said slots in said flange; and
        iii) a pair of hook and loop fasteners, wherein each said hook and loop fastener contains a hook tab attached to said pillow and a loop tab attached to a free end of one said strap, so that said straps can flip over said flange and be attached in a removable manner to said pillow, to allow said pillow to hang down on said outwardly slanted end wall.

2. A tanning pool as recited in claim 1, wherein said pillow includes a soft padding with a covering and being of a size to extend across said outwardly slanted end wall above the cool water placed within said elongated bed tray.

3. A tanning pool as recited in claim 2, further including:

a) a cup holder; and b) means for suspending said cup holder in an adjustable longitudinal manner on one of said outwardly slanted side walls of said elongated bed tray, so that when the person lies down in the cool water, said cup holder will provide a beverage for the person.

4. A tanning pool as recited in claim 3, wherein said cup holder includes a housing having a top aperture to receive a beverage receptacle therein.

5. A tanning pool as recited in claim 4, wherein said suspending means includes an inverted U-shaped bracket connected to said cup holder, so that said inverted U-shaped bracket can slide upon a top lip of said outwardly slanted side wall to longitudinally adjust said cup holder.

6. A tanning pool as recited in claim 5, further including:

a) said bottom wall of said elongated bed tray having a drain hole therethrough; and b) a drain cap placed in said drain hole, so when the cool water is to be drained therefrom, said drain cap will be manually removed from said drain hole.

7. A tanning pool as recited in claim 6, wherein said elongated bed tray is fabricated out of a transparent durable hard plastic material, being sturdy enough to hold the cool water therein and light enough to store away and be used over and over again.

8. A tanning pool as recited in claim 1, further including:

a) a cup holder; and b) means for suspending said cup holder in an adjustable longitudinal manner on one of said outwardly slanted side walls of said elongated bed tray, so that when the person lies down in the cool water, said cup holder will provide a beverage for the person.

9. A tanning pool as recited in claim 8, wherein said cup holder includes a housing having a top aperture to receive a beverage receptacle therein.

10. A tanning pool as recited in claim 8, wherein said suspending means includes an inverted U-shaped bracket connected to said cup holder, so that said inverted U-shaped bracket can slide upon a top lip of said outwardly slanted side wall to longitudinally adjust said cup holder.

11. A tanning pool as recited in claim 1, further including:

a) said bottom wall of said elongated bed tray having a drain hole therethrough; and b) a drain cap placed in said drain hole, so when the cool water is to be drained therefrom, said drain cap will be manually removed from said drain hole.

12. A tanning pool as recited in claim 1, wherein said elongated bed tray is fabricated out of a transparent durable hard plastic material, being sturdy enough to hold the cool water therein and light enough to store away and be used over and over again.

\* \* \* \* \*